United States Patent [19]

Johnson

[11] 4,338,162

[45] Jul. 6, 1982

[54] INHIBITOR FOR THE POLYMERIZATION OF A 2-ISOCYANATOALKYL ESTER OF AN α, β-ETHYLENICALLY UNSATURATED CARBOXYLIC ACID

[75] Inventor: Mark R. Johnson, Midland, Mich.

[73] Assignee: The Dow Chemical Company, Midland, Mich.

[21] Appl. No.: 216,694

[22] Filed: Dec. 15, 1980

[51] Int. Cl.$^3$ ............................................... B01D 3/34
[52] U.S. Cl. .................................. 203/8; 260/453 SP; 260/453 PH
[58] Field of Search .................. 260/453 SP, 453 PH; 203/8, 9

[56] References Cited

U.S. PATENT DOCUMENTS 3,964,978  6/1976  Watson ................................... 203/9
3,964,979  6/1976  Watson ................................... 203/9

OTHER PUBLICATIONS

J. F. Villa et al., *Syn. React. Inorg. Metal-Org. Chem.*, 6(1), pp. 59–63, (1976).

*Primary Examiner*—Frank Sever
*Attorney, Agent, or Firm*—Charles J. Enright

[57] ABSTRACT

Nitrogen oxides have been found to be effective to inhibit during distillation the vinyl polymerization of a 2-isocyanatoalkyl ester of an unsaturated carboxylic acid. For example, crude 2-isocyanatoethyl methacrylate was sparged with nitric oxide in nitrogen gas during distillation at 90° C., so as to effect a concentration of nitric oxide in the gas phase of 376 parts per million by weight. Essentially pure 2-isocyanatoethyl methacrylate was recovered in 70 percent yield.

7 Claims, No Drawings

INHIBITOR FOR THE POLYMERIZATION OF A 2-ISOCYANATOALKYL ESTER OF AN α,β-ETHYLENICALLY UNSATURATED CARBOXYLIC ACID

BACKGROUND OF THE INVENTION

This invention relates to the use of gaseous nitrogen dioxide or nitric oxide to inhibit the vinyl polymerization of a 2-isocyanatoalkyl ester of an α,β-ethylenically unsaturated carboxylic acid.

Certain conventional polymerization inhibitors have been used to inhibit during distillation the vinyl polymerization of a 2-isocyanatoalkyl ester of an α,β-ethylenically unsaturated carboxylic acid. For example, European Patent Office Application No. 78100156.5, Publication No. 144, published Jan. 10, 1979, discloses the use of phenothiazine to inhibit the polymerization of 2-isocyanatoethyl methacrylate during distillation.

While conventional polymerization inhibitors are generally effective in inhibiting polymerization of 2-isocyanatoalkyl esters during storage, they have not proven as effective during the distillation of the isocyanatoalkyl ester. In particular, these isocyanatoalkyl esters are susceptible to the formation of a hard, brittle, highly cross-linked polymer, which is referred to as "popcorn polymer" in the prior art because of its physical appearance. This popcorn polymer is especially deleterious, because once formed it tends to initiate further polymerization.

Relatively volatile inhibitors, such as p-methoxyphenol, have been employed during the distillation of 2-isocyanatoalkyl methacrylate to inhibit polymer formation in the gas phase and in the distillate. However, these volatile inhibitors have been observed to be relatively ineffective as polymerization inhibitors in this application.

Nitrogen oxides are known in the art to inhibit the polymerization of certain unsaturated compounds. U.S. Pat. No. 3,964,978 discloses the distillation of vinyl aromatic compounds in the presence of nitrogen dioxide to inhibit polymerization. U.S. Pat. No. 3,964,979 teaches the use of nitric oxide to inhibit the polymerization of vinyl aromatic compounds during distillation. British Patent No. 1,265,419 teaches that acrylic acid can be distilled in the presence of nitric oxide in the gas phase and phenothiazine in the liquid phase to minimize polymerization. However, the presence of nitrogen dioxide is taught to promote the polymerization of acrylic acid and to discolor the distillate.

Nitric oxide is disclosed by J. F. Villa and H. B. Powell, *Syn. React. Inorg. Metal-Org. Chem.*, 6, pp. 59–63 (1976), to catalyze the trimerization of certain aliphatic isocyanates. This disclosure suggests that nitric oxide would not be suitable as a polymerization inhibitor for a 2-isocyanatoalkyl ester.

SUMMARY OF THE INVENTION

This invention is an improved process for distilling a 2-isocyanatoalkyl ester of an α,β-ethylenically unsaturated carboxylic acid from a liquid mixture, comprising distilling the isocyanatoalkyl ester in the presence of an amount of gaseous nitric oxide or nitrogen dioxide effective to inhibit the vinyl polymerization of the isocyanatoalkyl ester. An "effective amount" of the nitrogen oxide is an amount which reduces the polymerization of the isocyanatoalkyl ester compared to the polymerization which occurs at the same conditions in the absence of the nitrogen oxide.

DETAILED DESCRIPTION OF THE INVENTION

The 2-isocyanatoalkyl esters of α,β-ethylenically unsaturated carboxylic acids form a known class of compounds, which can be represented by the formula I

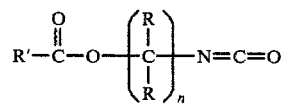

wherein each R is independently hydrogen, alkyl, alkenyl, alkoxy, alkaryl, aralkyl or aryl; R' is alkenyl; and n is 2 or 3. Of course, R can represent a wide variety of moieties, such as, methyl, ethyl, cyclohexyl, isopropenyl, vinyl, ethoxy, tolyl, phenylethyl or phenyl. Preferably, R is hydrogen and n is 2. Preferably, R' is vinyl or isopropenyl, more preferably isopropenyl. Hereafter, the compound of formula I will be referred to as an isocyanatoalkyl ester for the sake of brevity.

The isocyanatoalkyl ester can be present in any mixture from which it can be separated by distillation, so long as said mixture is substantially inert in the subject reaction. In order to conserve the nitrogen oxides added, diluents which may react with the nitrogen oxides are advantageously avoided. In one preferred embodiment, the isocyanatoalkyl ester to be distilled is prepared by reacting a 2-alkenyl-2-oxazoline or 2-alkenyl-2-oxazine in a water-immiscible solvent with phosgene in the presence of an aqueous hydrogen chloride acceptor, as is described in British Pat. No. 1,252,099. On completion of the phosgenation reaction, the organic phase containing the 2-isocyanatoalkyl ester is conveniently separated and optionally dried with a conventional drying agent, such as CaCl$_2$ or zeolite. The 2-isocyanatoalkyl ester of the unsaturated acid is then separated by distillation in the presence of a nitrogen oxide, as is disclosed hereinafter.

Nitrogen dioxide and nitric oxide, which are used as vinyl polymerization inhibitors herein, are both well-known compounds. For the sake of brevity these two polymerization inhibitors are hereafter referred to as nitrogen oxides. Either one of these nitrogen oxides, a mixture of such oxides or a diluent gas containing at least one of these oxides of nitrogen can be employed to inhibit polymerization. Nitric oxide is preferred as a polymerization inhibitor because it adds fewer colored impurities to the typically colorless distilled isocyanatoalkyl ester than the other nitrogen oxides. Surprisingly, no isocyanate trimer is observed in the isocyanatoalkyl ester following treatment with nitric oxide. Any gaseous diluent used with the nitrogen oxides should be inert in the instant reaction. Preferably, the diluent gas is substantially free of oxygen and water, more preferably the diluent gas, if present, is nitrogen.

The nitrogen oxide can operably be introduced in the region immediately above the liquid mass to be distilled to inhibit polymerization in the gas phase and in the liquid which condenses overhead. However, care must be taken in this embodiment to insure that the nitrogen oxide permeates the space above the medium or polymerization can occur. Of course, where a nitrogen oxide is not introduced to the liquid medium, a polymerization inhibitor should also be employed in the liquid. However, some of the oxides of nitrogen interact with other polymerization inhibitors to produce colored impurities. For example, p-methoxyphenol reacts with nitric oxide to produce a yellow-colored impurity, which will codistill with the isocyanatoalkyl ester. Less volatile polymerization inhibitors, such as phenothiazine, may also form colored impurities, but these colored impurities typically will not distill with the isocyanatoalkyl ester. It is preferred, therefore, to sparge the nitrogen oxide through the liquid mixture during distillation and to use a polymerization inhibitor in the mixture which is significantly less volatile than the isocyanatoalkyl ester.

If the distillation is conducted in a continuous process, the nitrogen oxide can conveniently be added to the incoming mixture containing the isocyanatoalkyl ester. The gaseous nitrogen oxides are virtually insoluble in the isocyanatoalkyl ester and these gases can be readily recovered and recycled. Generally, the inhibitor is gradually depleted during operation, but with recycle the intermittent replacement of only small amounts of the oxides of nitrogen is generally necessary.

The concentration of nitrogen oxides necessary to inhibit polymerization varies over a wide range dependent upon numerous factors, including the identity of the nitrogen oxide and the isocyanatoalkyl ester, the distillation temperature, the distillation pressure, residence time and the amount of reflux. Even the purity of the isocyanatoalkyl ester affects the formation of polymers, as a crude starting material appears in general less susceptible to the formation of popcorn polymer during distillation than a comparatively pure isocyanatoalkyl ester. Generally, a concentration of nitric oxide in the gas phase immediately above the liquid medium of at least about 0.01, preferably at least about 0.02, more preferably at least about 0.1 percent by weight, is effective to inhibit polymerization. At or near the minimum effective concentration care must be taken to see that the concentration is maintained uniformly above the liquid medium or else polymerization can occur. One convenient method distributing the nitrogen oxide uniformly in a large volume is to introduce the nitrogen oxide to the liquid in a diluent gas. The upper limit on the concentration of nitrogen oxide is determined primarily by economic considerations. The concentration of nitrogen oxides is preferably less than about 20 percent, more preferably less than about 3 percent by weight of the gases above the liquid distilled. At concentrations of nitrogen oxide greater than about 2 percent by weight the distillate may be visibly colored.

The manner in which the distillation is carried out is not critical. The distillation is advantageously conducted at reduced pressure, so as to avoid distillation at temperatures which are deleterious to the isocyanatoalkyl ester. The distillation vessel should be closed, because some isocyanatoalkyl esters are very toxic, as are the oxides of nitrogen. Impurities which are lower boiling than the isocyanatoalkyl ester are conveniently distilled before the isocyanatoalkyl ester. Azeotropic mixtures can be created to modify the order of distillation, if desired.

The temperature of the liquid during distillation is preferably from about 65° C. to about 110° C., more preferably from about 80° C. to about 95° C. Higher temperatures than those in the preferred range, though operable, can result in poor separation and substantial decomposition or polymerization of the isocyanatoalkyl ester at long residence times. Lower temperatures are not generally operable to distill the isocyanatoalkyl ester, even when distillation is attempted under vacuum. Preferably, the pressure over the liquid to be distilled is from about 5 to about 15 millimeters of mercury during distillation.

The following examples are presented to illustrate the process of this invention, but are not to be taken as limiting its scope. All parts and percentages are by weight unless otherwise indicated.

EXAMPLE 1

To a round-bottom flask equipped with a 6-inch, straight tube distillation column topped with a distillation head, a means for stirring and a means for measuring temperature, is charged 121 grams of crude 2-isocyanatoethyl methacrylate (IEM) containing 82.2 percent IEM, 0.6 percent methylene chloride, 1080 parts per million (ppm) phenothiazine, less than 1 percent of an epoxy resin, and a remaining amount of relatively non-volatile impurities resulting from the preparation of IEM. The epoxy resin reacts during distillation with the hydrolyzable chloride present to eliminate this impurity from the distillate.

The flask is heated to 95° C. under a pressure of 10 mm of mercury, while the liquid is sparged with 20 cubic centimeters per minute of a nitrogen gas containing 0.8 percent nitric oxide. The IEM is refluxed for 1.25 hours and then distilled for 2 hours. Assuming a constant rate of distillation, the concentration of nitric oxide in the gas phase is 376 ppm.

The distillate recovered is analyzed by conventional gas and liquid chromatographic techniques and is found to be essentially pure monomeric IEM. The 85 grams of distillate recovered represents a yield of 70 percent. The undistilled tars are clear fluids. No popcorn polymer is observed.

COMPARATIVE EXPERIMENT

In the manner described in Example 1, 50 grams of crude IEM is refluxed at 95° C. under a pressure of 10 mm of mercury, except that no nitric oxide is introduced. After 15 minutes of heating, popcorn polymer is observed in the column and the flask. After an additional hour, the entire contents of the flask polymerize.

EXAMPLE 2

In a manner otherwise identical to Example 1, pure nitric oxide is sparged through the crude IEM, while the IEM is first refluxed at 95° C. for 1 hour and then distilled over a period of 2 hours. No popcorn polymer was observed in either the distillate or the undistilled material.

EXAMPLE 3

In a manner otherwise similar to Example 2, 204.4 grams of crude IEM, containing 86.6 percent IEM and 700 ppm phenothiazine, are refluxed at 90° C. for 1 hour and then distilled. During reflux and distillation, a nitrogen gas stream containing 0.8 percent nitric oxide is introduced to the distillation vessel immediately above the liquid medium. Two and one-half hours after the reflux is initiated, all of the material remaining in the flask is popcorn polymer. The distillate contains 112.5 grams of essentially pure IEM, representing a yield of 55 percent.

EXAMPLE 4

In a manner similar to Example 1, 151 grams of crude IEM, containing 81 percent IEM, 1000 ppm phenothiazine and small amounts of methylene chloride and an epoxy resin, are refluxed at 92° C. under a pressure of 9 millimeters of mercury, while a gaseous mixture containing 0.16 percent nitrogen dioxide in nitrogen is sparged through the liquid. The gas is passed through the liquid at a rate of 168.8 cubic centimeters per minute. After 2 hours, distillation of the gas-sparged liquid is initiated. Over a period of 3 hours, 85.6 grams of essentially pure IEM is recovered in the distillate, representing a yield of 70 percent. The undistilled residue remains fluid and no popcorn polymer is produced in the system.

What is claimed is:

1. In a process for distilling a 2-isocyanatoalkyl ester of an $\alpha,\beta$-ethylenically unsaturated carboxylic acid from a liquid mixture, the improvement comprising distilling the isocyanatoalkyl ester in the presence of an amount of gaseous nitrogen oxide effective to inhibit the vinyl polymerization of the isocyanatoalkyl ester.

2. The process as described in claim 1 wherein the nitrogen oxide is nitric oxide.

3. The process as described in claim 2 wherein the distillation is conducted in an oxygen-free atmosphere.

4. The process as described in claim 2 wherein the nitric oxide is sparged through the liquid mixture.

5. The process as described in claim 4 wherein the concentration of nitric oxide in the gas phase immediately above the liquid is from about 0.01 to about 3 percent by weight.

6. The process as described in claim 2 wherein the isocyanatoalkyl ester is 2-isocyanatoethyl methacrylate.

7. The process as described in claim 6 wherein the 2-isocyanatoethyl methacrylate to be distilled is present in the organic solution resulting from the reaction of 2-isopropenyl-2-oxazoline with phosgene in a water-immiscible organic solvent in the presence of an aqueous hydrogen chloride acceptor.

* * * * *